(12) United States Patent
Maycox et al.

(10) Patent No.: US 7,038,105 B2
(45) Date of Patent: May 2, 2006

(54) TRANSGENIC MOUSE EDG2 KNOCKOUT MODEL

(75) Inventors: Peter Ronald Maycox, Harlow (GB); Charles Alan Reavill, Harlow (GB)

(73) Assignee: Smithkline Beecham Corporation, Philadelphia, PA (US)

(*) Notice: Subject to any disclaimer, the term of this patent is extended or adjusted under 35 U.S.C. 154(b) by 357 days.

(21) Appl. No.: 10/225,835

(22) Filed: Aug. 22, 2002

(65) Prior Publication Data

US 2003/0056236 A1    Mar. 20, 2003

(30) Foreign Application Priority Data

Aug. 22, 2001  (GB) ................................. 0120349.6

(51) Int. Cl.
   G01N 33/00    (2006.01)
   A01K 67/027   (2006.01)

(52) U.S. Cl. ............................................ 800/3; 800/18

(58) Field of Classification Search .................... 800/3, 800/8, 18
   See application file for complete search history.

(56) References Cited

U.S. PATENT DOCUMENTS

2002/0061558 A1  5/2002  Elshourbagy et al.
2002/0090691 A1  7/2002  Elshourbagy et al.

FOREIGN PATENT DOCUMENTS

CA    2199455    9/1998

OTHER PUBLICATIONS

Prelle, K. 1999, Establishment of pluripotent cell lines from vertebrate species-present status and future prosopects, Cells Tissues Organs, vol. 165, pp. 220-236.*
Campbell and Wilmut, 1997, Totipotency or multipotency of cultured cells: applications and progress, Theriogenology, vol. 47, pp. 63-72.*
Wheeler, M.B. 2001, Transgenic technology and applications in swine. Theriogenology, vol. 56, pp. 1345-1369.*
Contos et al., "Requirement for the 1pA1 lysophosphatidic acid receptor gene in normal suckling behavior," *Proc. Nat'l. Acad. Sci. USA* 97(24):13384-13389 (Nov. 2000).
Dulawa et al., "Serotonin-1B receptor modulation of startle reactivity, habituation, and prepulse inhibition in wild-type and serotonin-1B knockout mice," *Psychopharmacology* 132(2):125-134 (1997).
Muller, "Ten years of gene targeting: Targeted mouse mutants, from vector design to phenotype analysis," *Mechanisms of Development, Elsevier Science Ireland* 82 (1-2):3-21 (Apr. 1999).
Bickerdike et al., "Social isolation attenuates rat forebrain 5-HT release induced by KCl stimulation and exposure to a novel environment," *Behavioural Pharmacology* 4:231-236 (1993).
Braff et al., "Sensorimotor gating and schizophrenia," *Arch. Gen. Psychiatry* 47(2):181-188 (1990).
Choi et al., "Transgenic mice containing a human heavy chain immunoglobulin gene fragment cloned in a yeast artificial chromosome," *Nature Genet.* 4:117-123 (1993).
Cilia et al., "Long-term evaluation of isolation-rearing induced prepulse inhibition deficits in rats," *Psychopharmacology* 156:327-337 (2001).
Costantini et al., "Introduction of a rabbit β-globin gene into the mouse germ line," *Nature* 294:92(Nov. 1981).
Durson et al., "Effects of clozapine and typical antipsychotic drugs on plasma 5-HT turnover and impulsivity in patients with schizophrenia: a cross-sectional study," *Journal of Psychiatry and Neuroscience* 25(4):347:352 (2000).
Fletcher et al., "Reduced brain serotonin activity disrupts prepulse inhibition of the acoustic startle reflex: effects of 5,7-dihydroxytrptamine and p-chlorophenylalanine," *Neuropsychopharmacology* 24(4):399-409 (Apr. 2001).
Fukushima et al., "The LPA receptors," *Prostaglandins & Other Lipid Mediators* 64:21-32 (2001).
Hervieu et al., "Gene expression and protein distribution of the Orexin-1 receptor in the rat brain and spinal cord," *Neuroscience* 103(3):777-797 (2001).
Kehne et al., "5-HT modulation of auditory and visual sensorimotor gating: I. Effects of 5-HT releasers on sound and light prepulse inhibition in Wistar rats," *Psychopharmacology* 124:95-106 (1996).
Mauvais-Jarvis et al., "Understanding the pathogenesis and treatment of insulin resistance and type 2 diabetes mellitus: what can we learn from transgenic and knockout mice," *Diabetes and Metabolism* 26:433-448 (2000).
Robbins et al., "Behavioural and neurochemical effects of early social deprivation in the rat," *J. Psychopharmacology* 10(1):39-47 (1996).
Strauss et al., "Germ line transmission of a yeast artificial chromosome spanning the Murine $\alpha_1(1)$ collagen locus," *Science* 259:1904-1907 (Mar. 1993).
Wilkinson et al., "Social isolation in the rat produces developmentally specific deficits in prepulse inhibition of the acoustic startle response without disrupting latent inhibition," *Neuropsychopharmacology* 10(1):61-72 (1994).
Wright et al., "Effect of isolation-rearing on 5-HT release in the rat frontal cortex," *J. Neuroscience Methods* 29:283 (1989).

* cited by examiner (Continued)

*Primary Examiner*—Scott D. Priebe
*Assistant Examiner*—Valarie Bertoglio
(74) *Attorney, Agent, or Firm*—Michael M. Conger

(57) ABSTRACT

The present invention provides a transgenic non-human animal and method for using the same in evaluating a therapeutic agent for use in the treatment of Schizophrenia. More specifically, the invention is directed to a transgenic non-human animal which is incapable of expressing functional EDG2 protein. A theraupeutic agent is administered to the transgenic non-human animal incapable of expressing functional EDG2 protein and the effect of the agent on the animal is evaluated.

3 Claims, 7 Drawing Sheets

Disruption of the EDG2 gene by homologous recombination.

Prepulse Inhibition in Male and Female EDG2 -/- and Wild Type Mice
Prepulse = 80dB tone; Pulse = 110dB White noise C57 = Wild; EDG2 = -/-; F = Female; M = Male Prepulse Inhibition in Male and Female EDG2 -/- and Wild Type Mice
Prepulse = 90dB tone; Pulse = 110dB White noise C57 = Wild; EDG2 = -/-; F = Female; M = Male Startle Response in Male and Female EDG2 -/- and Wild Type Mice
Pulse = 80dB C57 = Wild; EDG2 = -/-; F = Female; M = Male Startle Response in Male and Female EDG2 -/- and Wild Type Mice
Pulse = 90dB C57 = Wild; EDG2 = -/-; F = Female; M = Male

TRANSGENIC MOUSE EDG2 KNOCKOUT MODEL

CROSS-REFERENCE TO RELATED APPLICATIONS

This application claims priority from Great Britain Application No. 0120349.6 filed in the United Kingdom on Aug. 22, 2001.

BACKGROUND OF THE INVENTION

One of the symptoms of schizophrenia is a decrease in the capacity to filter and process novel sensory or cognitive stimuli. This can be demonstrated in both animals and humans by using a paradigm called prepulse inhibition (PPI). If an intense, sudden stimulus is presented, it elicits a startle response, which can be monitored in animals by measuring the flinching of the animal. If the startling stimulus is preceded by a weak prepulse, then the startle response is inhibited. schizophrenia patients show a deficient or weak PPI, reflecting a lack of inhibitory function or sensorimotor gating (Braff et al Arch. Gen. Phychiatry 1990; 47(2) PP 181–8). Prepulse inhibition in animals has been used as a model for screening drugs to treat schizophrenia. If the phenotype of a weak PPI can be reversed in an animal model by a drug, then it is indicative that the drug could be used to treat schizophrenia. However, no models currently exist wherein PPI develops naturally as the animal matures. Current models are generated by inducing the phenotype either by external stimuli, for example pre or post-weaning social isolation, or chemically by compounds such as apomorphine or quinpirole. A neurodevelopmental model that naturally develops some of the symptoms of schizophrenia such as PPI would provide an extremely useful tool for screening compounds to treat schizophrenia. Such a model, as presented herein, provides advantages over the prior art in that it mimics the natural development of schizophrenia, rather than having to be artificially induced.

Endothelial differentiation gene 2 (EDG2) has enriched embryonic expression in the developing cerebral cortex and dorsal olfactory bulb, and postnatal expression in myelinating glia including Schwann cells and other oligodendrocytes. It is a lysophosphatidic acid receptor, and has been shown to couple to at least two different G-proteins: $G_{i/o}$ and a pertussis toxin insensitive G protein that appears to be $G_{12}$ or $G_{13}$. (Fukushima and Chun, Prostaglandins & other Lipid Mediators (2001) 64 pp21–32). However, no role has been postulated for EDG2 in schizophrenia. The present inventors have surprisingly managed to develop a developmental model for schizophrenia by a targeted knockout of the EDG2 gene.

SUMMARY OF THE INVENTION

The present inventors have generated a transgenic non-human animal model of schizophrenia. They have found that the use of a construct which produces a targeted disruption in the EDG2 locus such that no functional EDG2 is produced, results in a transgenic non-human animal which naturally develops a convincing schizophrenia phenotype comprising a deficit in prepulse inhibition. Such animals allow compounds and other therapeutic regimens to be screened and evaluated in vivo as possible treatments for schizophrenia. Accordingly, the present invention provides a method of evaluating a therapeutic agent for use in the treatment of schizophrenia, which method comprises:

i) administering the said agent to a transgenic non-human animal which is incapable of expressing functional EDG2 protein and
ii) evaluating the effect of the said agent on the transgenic non-human animal.

Preferably, said non-human transgenic animal comprises a targeted disruption in the EDG2 gene such that no functional EDG2 protein is expressed.

The present invention also provides a kit for screening agents for use in the treatment of Schizophrenia, which kit comprises a transgenic non-human animal incapable of expressing functional EDG2 protein, and a means for determining whether a therapuetic agent can ameliorate the phenotype associated with non-expression of functional EDG2 protein.

The present invention further provides a method of treating schizophrenia comprising administration of a therapuetically effective amount of a therapeutic agent identified in a screening method as herein described.

Further provided is the use of a compound identified by a screening method as herein described for the treatment of schizophrenia.

Further provided is the use of a compound identified by a screening method as herein described in the manufacture of a medicament for the treatment of schizophrenia

DETAILED DESCRIPTION OF THE INVENTION

Figure 1:
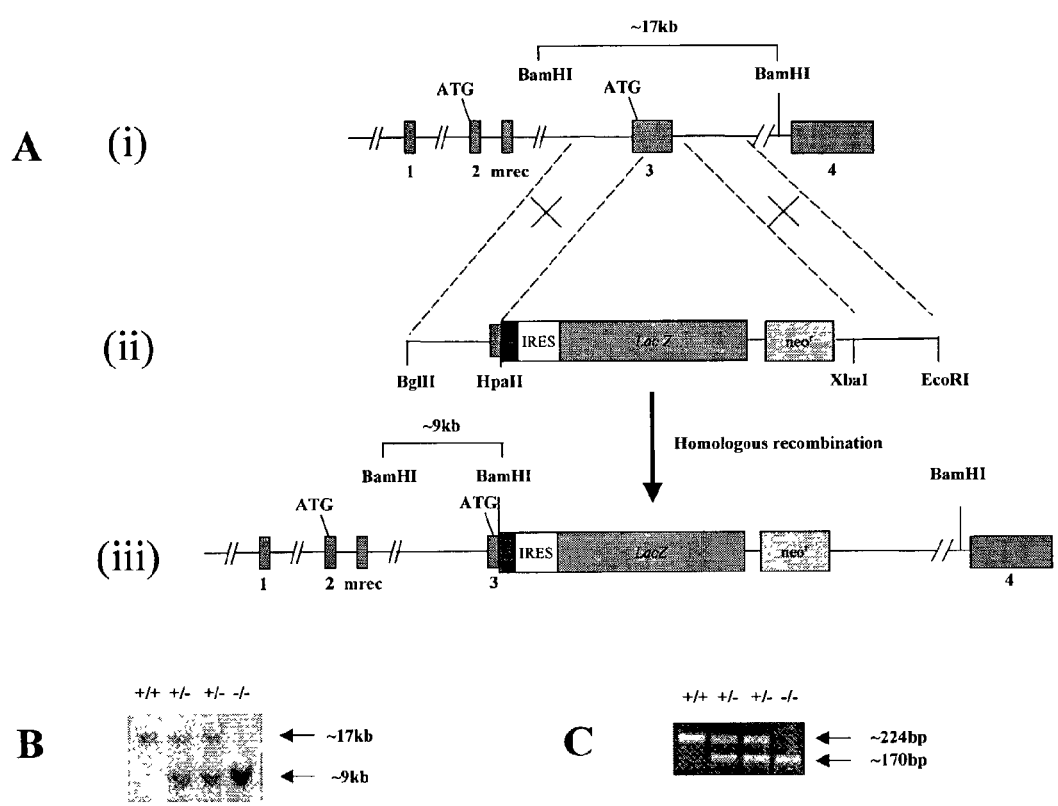
FIG. 1 shows the targeting strategy used (1A), and the results of genotyping of two generations of transgenic mice—N1F1 (FIG. 1B) and N5F1 (FIG. 1C).

The term transgene as used herein is intended to mean a nucleic acid vector which comprises nucleotide sequences which have been manipulated in-vitro and subsequently introduced into the genome of a species such that it is stably and heritably maintained in that genome. A transgenic animal is an animal that contains such a transgene within its cells. A "knock-out" animal is a sub family of transgenic animals, and is an animal wherein the transgenic construct has caused an endogenous gene not to be expressed. The present invention provides a method of evaluating compounds for their efficacy in the treatment of schizophrenia, which method involves the use of a transgenic non-human animal which is incapable of expressing functional EDG2 protein. This may be a natural incapability, or it may be engineered by genetic techniques. Preferably, it is engineered, and particularly preferably, said non-human animal contains a targeted disruption in the EDG2 locus such that the non-human animal does not express functional EDG2 protein. The targeted disruption may be anywhere in the EDG2 gene, subject only to the requirement that it inhibits expression of functional EDG2 protein. This may be achieved, for example, by inhibiting expression of the protein completely, or by causing expression of a truncated protein, or a protein that is mutated such that it cannot perform its function, for example by engineering amino acid mutations within the active site. In a preferred embodiment, the targeted disruption is such that a truncated, non-functional EDG2 protein is translated. Further preferred is when the disruption is caused by the insertion of a stop codon into an exon. In a particularly preferred embodiment, the stop codon is inserted into exon 3 such that truncated, non-functional forms of both EDG2, and the variant of EDG2 also contained within the EDG2 locus, the orphan receptor mrec-1 are expressed.

The targeted disruption of the EDG2 locus is caused by the integration into the genome of the transgenic construct. This integration is preferably achieved by homologous recombination. In this method, two regions of nucleotide sequence are designed that are homologous to the regions of the gene upstream (5') or downstream (3') of the target region. If recombination between the homologous areas of the gene and the transgenic construct occurs, then the target region of the gene is replaced with the region of the transgenic construct contained between the two areas of homology. This technique is described in Joyner, A L. *Gene Targeting—A Practical Approach*(*Second Edition*). (Oxford Univ. Press, Oxford, 2000).

It will be apparent to a person skilled in the art that any desired nucleotide sequence may thus be introduced into the target region of the gene by including the desired sequence between the areas of homology on the transgenic construct. Thus, for example, the construct may be engineered to contain a reporter gene such as luciferase, green fluorescent protein or derivatives thereof, or a β galactosidase gene. Such a reporter gene is preferably engineered to be immediately downstream of an internal ribosomal entry site such that transcription of the reporter gene occurs. The site of integration of the transgene in the non-human transgenic animal can be determined by observing and/or measuring expression of the reporter gene. Preferably, the transgenic construct also comprises a selectable marker such as an antibiotic resistance marker, preferably neomycin resistance. The marker enables selection of those cells that have taken up the transgenic construct following the transfection of the construct into cells.

The assembly of the transgenic construct follows standard cloning techniques, that are well known in the art (for example see Sambrook et al, Molecular Cloning: A laboratory Manual, $2^{nd}$ Ed. Cold Spring Harbor Laboratory Press, Cold Spring Harbor, N.Y. (1989)). The areas of homology designed to the regions upstream and downstream of the target region, and any other desired components such as stop codons, an IRES, a selectable expression marker or a reporter gene can then be inserted into a cloning vector by restriction digest and ligation. Suitable cloning vectors for the assembly of transgenes are those which provide for acceptable yields of DNA. Any commercially available plasmid vector or phage that can carry the desired regions of homology and which can be manipulated to contain a selection marker is suitable.

The transgenic non-human animal of the invention may be any animal that comprises an endogenous EDG2 gene. By endogenous is meant that the gene is comprised in the genome of that animal, and would under normal circumstances be expressed to produce EDG2 protein. Preferably, the animal is a mammal. More preferably it is a rodent, and particularly preferred is when the transgenic animal is a mouse or a rat.

The non-human transgenic animals of the invention may be generated by the use of any appropriate protocol. A suitable method comprises:
    making a suitable cell of the invention;
    allowing the cell to develop into an animal of the invention; and
    optionally, breeding the animal true.

Transgenic non-human animals of the invention may be produced by methods well known in the art. There are a number of techniques that permit the introduction of genetic material, such as a transgene, into the germline. The most commonly used, and preferred protocol comprises direct injection of the transgene into the male pronucleus of the fertilised egg (Hogan et al., Manipulating the mouse embryo (A laboratory manual) Second edition, CSHL Press 1994), resulting in the random integration into one locus of a varying number of copies, usually in a head to tail array (Costantini and Lacy, Nature 294, 92, 1981). The injected eggs are then re-transferred into the uteri of pseudo-pregnant recipient mothers. Some of the resulting offspring may have one or several copies of the transgene integrated into their genomes, usually in one integration site. These "founder" animals are then bred to establish transgenic lines and to back-cross into the genetic background of choice. It is preferable to have the transgene insertion on both chromosomes (homozygosity) as this obviates the need for repeated genotyping in the course of routine mouse husbandry.

Alternatively, for the production of transgenic mice, transgenes can be introduced via embryonic stem (ES) cells, using electroporation, retroviral vectors or lipofection for gene transfer. This is followed by the random insertion into the genome of the pluripotent embryonic stem (ES) cells, followed by the production of chimeric mice and subsequent germline transmission. Transgenes of up to several hundred kilobases of rodentian DNA have been used to produce transgenic mice in this manner (for example Choi et al., Nature Genet. 4, 117–123 (1993); Strauss et al., Science 259, 1904–07 (1993)).

The transgenic animals can be subsequently tested to ensure the required genotypic change has been effected, in any suitable fashion. This can be done by, for example, detecting the presence of the transgene by PCR with specific primers, or by Southern blotting of tail DNA with a specific probe. Testing for homologous recombination leading to insertion of the transgene is done by restriction digestion. The band sizes seen if recombination has taken place are different to those seen if it has not. Suitable methods for this procedure are given in the examples. Testing for homozygosity of the transgene insertion may be carried out using quantitative Southern blotting to detect a twofold difference in signal strength between hetero- and homozygous transgenic animals . Confirmation that the EDG2 gene is not being expressed can be carried out by immunohistochemical techniques, as described in the examples. EDG2 has been identified as a lysophosphatidic acid (LPA) receptor, and confirmation that the EDG2 gene is not being expressed can be achieved by measuring response to LPA.

Once the desired genotype has been confirmed the transgenic animal line can be subjected to various tests to determine the phenotype. The tests involved in this phenotypic characterisation depend on what genotypic change has been effected, and may include, for example, morphological, biochemical and behavioural studies. In particular, such phenotypic tests will involve testing for a pre-pulse inhibition deficit, or measuring for a decrease in 5-HIAA levels, or a decrease in the 5HIAA/5HT ratio as described in the examples.

The use of non-human animal models which overexpress or lack more than one gene can provide important insights into the interaction of different genetic loci in particular diseases, for example diabetes (Mauvais-Jarvis and Kahn, Diabetes and Metabolism, 26, 433–448, 2000). Consequently the interbreeding of the transgenic non-human animals of the present invention with non-human animal models which overexpress or underexpress a different gene may produce alternative and potentially superior animal models of diseases such as schizophrenia. Cross-breeding of the non-human EDG2 knockout transgenic animals of the invention with other transgenics or knockouts could also enable the identification of genes which pre-dispose for or protect against diseases such as schizophrenia. Such crosses, wherein one predecessor transgenic non-human animal demonstrates a schizophrenic phenotype as a result of non-expression of functional EDG2 may also be used as described herein.

The transgenic non-human animal may be used to screen for drugs which reverse the phenotype demonstrated, for example ameliorate the prepulse inhibition deficit, and hence may be useful in treating schizophrenia. The invention extends to such method of screening.

A method of evaluating a therapeutic agent for use in the treatment of Schizophrenia is therefore provided, which method comprises:

administering the said agent to a transgenic non-human animal which is incapable of expressing functional EDG2 protein and
i) evaluating the effect of the said agent on the transgenic non-human animal.

The effect of the therapuetic agent on the animal may be evaluated by determining whether the candidate substance causes a reversal, or ameliorates in any way any of the cellular or physiological changes caused by the condition. Such physiological changes preferably include a pre-pulse inhibition deficit, and a decrease in the 5HIAA/5HT ratio.

Suitable candidate substances which may be tested in the above methods include antibody products (for example, monoclonal and polyclonal antibodies, single chain antibodies, chimeric antibodies and CDR grafted antibodies). Furthermore, combinatorial libraries, defined chemical identities, small molecules, peptide and peptide mimetics, oligonucleotides and natural product libraries, such as display libraries (e.g. phage display libraries) may also be tested. The candidate substances may be chemical compounds. Batches of the candidate substances may be used in an initial screen of, for example, ten substances per reaction, and the substances of batches which show inhibition tested individually.

Compounds can be tested using the assays and tests used to characterise the invention. For example, after administration of any potential therapeutic agent, the response of the transgenic animal may be assessed by looking for an improvement in the pre-pulse inhibition deficit, or an increase in the 5HIAA/5HT ratio as described in the Examples.

Agents identified in the screening methods of the invention may be used to prevent or treat schizophrenia. The condition of a patient suffering from such a disease can therefore be improved by administration of such a product. The formulation of the product for use in preventing or treating the disease will depend upon factors such as the nature of the agent identified, the precise combination of symptoms, and the severity of the disease. Typically the agent is formulated for use with a pharmaceutically acceptable carrier or diluent. For example it may be formulated for intracranial, parenteral, intravenous, intramuscular, subcutaneous, transdermal or oral administration. A physician will be able to determine the required route of administration for each particular patient. The pharmaceutical carrier or diluent may be, for example, an isotonic solution.

The dose of product may be determined according to various parameters, especially according to the substance used; the age, weight and condition of the patient to be treated; the route of administration; the severity of the disease, and the required regimen. A suitable dose may however be from 0.1 to 100 mg/kg body weight such as 1 to 40 mg/kg body weight. Again, a physician will be able to determine the required route of administration and dosage for any particular patient.

The invention will now be further described by means of the following, non-limiting examples.

EXAMPLES

1. Generation of EDG2 Knockout Animals

For simultaneously knocking in the lac-Z reporter gene and targeted disruption of the EDG2 gene, homologous recombination was designed to result in the replacement of all but the first 51 bp of exon 3 of the EDG2 gene (and therefore almost all of the coding regions of the EDG2 and mrec transcripts) with a cassette containing the lacZ gene preceded by an internal ribosome entry site, downstream of which is a neomycin resistance gene cassette. The arms of homology were cloned from a 129SVJ genomic BAC library. The 5' arm was an approximately 4.2 kb/bgIII-HpaII restriction fragment (generated by joining a 4.0 kb BgIII restriction fragment to a 0.2 kb BgIII-HpaII restriction fragment) where the 5'BgIII site lies in intron 2 and the HpaII site lies in exon 3, 102 bp and 48 bp downstream of the EDG2 and mrec1.3 translation intiation codons respectively. The 3' arm of homology was an approximately 3.5 kb XbaI/EcoRI restriction fragment from within intron 3. The targeting strategy is demonstrated diagramatically in FIG. 1A. The arms of homology are indicated by the dotted lines.

Homologous recombination in neomycin resistant embryonic stem cells was confirmed by Southern blot of BamH1 digested genomic DNA. The 5' probe is an approximately 15. kb AccI restriction fragment which is derived from a 3.7 kb EcoRV/BgIII restriction fragment which lies immediately 5' to the 5' arm of homology. Homologous recombination is shown by the presence of a 9 kb BamHI fragment (shown on part iii of FIG. 1A), and wild type is shown by the presence of a 17 kb fragment (shown on part i of FIG. 1A). Approximately 1 in 20 G418 resistant clones had undergone homologous recombination. Three targeted clones were injected into C57Bl6/J-derived blastocysts. Male chimaeras were crossed with C57Bl6/J females to give N1F0 offspring, which were subsequently intecrossed to generate N1F1 offspring. Genotype analysis by Southern blot of tail DNA of the N1F1 offspring is shown in FIG. 1B.

In addition N1F0 offspring were successively backcrossed to C57Bl6/J females to generate N5F0 mices. These were intercrossed to create an N5F1 study population.

Genotype analysis during back-crossing and for the generation of the N5F1 study populatation was performed by PCR of tail DNA. Primers were designed to generate PCR products specific to the wild type (giving a product of 224 bp) and to the targeted locus (giving a product of 170 bp). Results from the genotype analysis of the N5F1 offspring is shown in FIG. 1C.

In order to confirm that EDG2 was not being expressed in the transgenic knockout mice, a rabbit polyclonal antiserum was raised against a C-terminal peptide of the mouse EDG2 sequence (LAGVHSNDHSVV-amide) as previously described (Hervieu G J, Cluderay J E, Harrison D C, Roberts J C, Leslie R A; Gene expression and protein distribution of the Orexin-1 receptor in the rat brain and spinal cord. Neuroscience. 2001;103,(3):777–797) and affinity purified using an affinity chromatography column with a Sulfolink matrix covalantly linked to the N-terminal Cysteine-extended immunogenic peptide. Immunohistochemistry was carried out using an avidin:biotin amplification technique as previously described (Herv et al supra).

Figure 7:
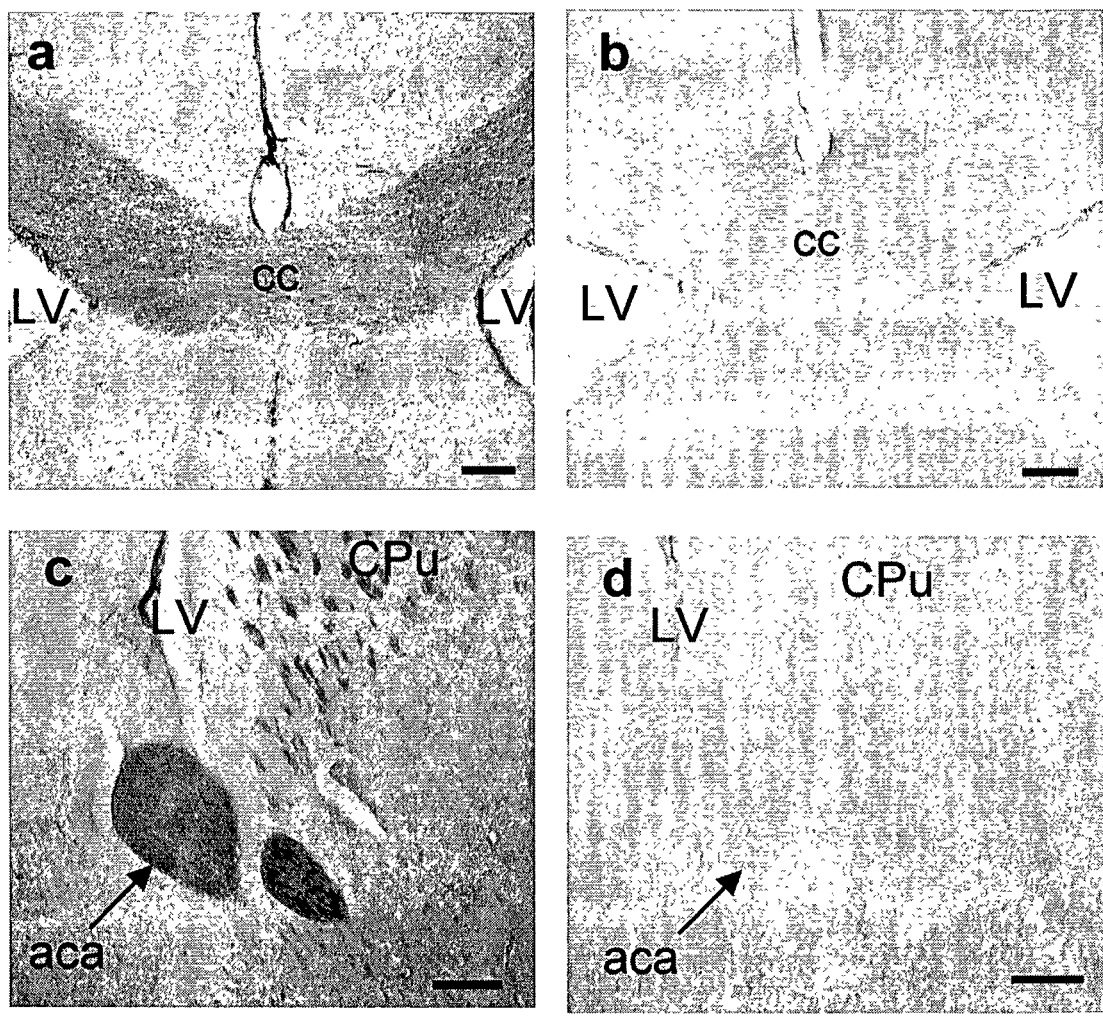
FIG. 7 shows confirmation by immunohistochemical techniques that the transgenic mice of the present invention do not express EDG2.

The results are shown in FIG. 7. This shows that in EDG2 +/+ homozygous control mice, immunoreactivity was observed in white matter tracts such as corpus callosum (a) and anterior commisure (c). This immunoreactivity was absent in the −/− homozygous knockout mice (b,d). The absence of the immunoreactivity demonstrates that no EDG2 was being expressed in the transgenic non-human animals of the invention.

Scale bars: 80 um. Abbreviations: aca, anterior commisure; cc, corpus callosum; CPu, caudate putamen; LV, lateral ventricle.

2. Pre-pulse Inhibition and Startle Analysis of EDG2 Knockout Mice

Heterozygous offspring N1 offspring were backcrossed 5 times to generate mice at N6 generation. These were interbred to produce the study cohort (N6F1). SHIRPA was used to assess the behavioural phenotype of 10 male and 10 female homozygous EDG2 knockout mice, and 10 male and 10 female wildtype littermates. Mice were housed in individual cages and maintained under a standard 12-hr light: dark cycle with food and water available ad libitum. Testing began when the mice were between 7 and 8 weeks of age.

The test chamber consisted of a perspex chamber with a moving base that was used to measure shifts in the subject's weight. The moving base was supported by 4 springs. Perspex walls mounted on the top face of a steel plate provided rigid support for a steel rod floor. The springs were positioned, one in each corner, to allow adequate movement of the base when startle movements occurred, and the measurement was performed by an accelerometer mounted on the metal plate (frequency response 0.2–500 Hz and linearity of 0.001–20 G). A sawdust tray was inserted in the space between the steel plate and the grid floor, being mounted on rods attached to the Perspex base plate. The test chamber enclosure was used to mount a light and speaker. The complete system incorporated 12 identical enclosures, and isolation between test chambers was performed by placing each chamber within a soundproof box (500×500× 500 mm) constructed from 2 mm aluminium plate and 2" acoustic foam. The front side of the box was hinged to give access to the test chamber.

Procedure for Prepulse Inhibition

Mice were individually placed in a startle chamber and left for a pretrial delay of at least 1 minute. The mice were then exposed to a series of acoustic stimuli which were configured in six blocks of trials. The following block is an example of how the trials within a block were configured:
PP(T/12/80/10), ISD 100, P(W/110/10)×5 P(W/110/10)×3

In this convention the block was composed of 5 trials of a prepulse (PP) tone (T), 12 kHz and 80 dB for 10 msec followed by an interstimulus delay (ISD) of 100 msec followed by a pulse (P) of white noise (W), 110 dB for 10 msec; and 3 trials of a pulse (P) of white noise (W), 110 dB for 10 msec. The order of the eight trials within each block were randomised. The house light was on throughout, and there was a constant background of 60 dB white noise. The intertrial delay was set to a minimum of 15 sec and maximum of 30 sec with the trial condition set to "quiet". Under these conditions, there was a minimum trial delay of 15 sec following the preceding trial after which the next trial was triggered at the moment when the subject was not moving within the following 15 sec.

There were six blocks with prepulse of 90 dB which were run in the following order:
PP(T/20/90/10), ISD 100, P(W/110/10)×5 P(W/110/10)×3
PP(T/4/90/10), ISD 100, P(W/110/10)×5 P(W/110/10)×3
PP(T/12/90/10), ISD 100, P(W/110/10)×5 P(W/110/10)×3
PP(T/12/90/10), ISD 100, P(W/110/10)×5 P(W/110/10)×3
PP(T/4/90/10), ISD 100, P(W/110/10)×5 P(W/110/10)×3
PP(T/20/90/10), ISD 100, P(W/110/10)×5 P(W/110/10)×3

When all the mice had been tested, the tests were repeated at a prepulse of 80 dB:
PP(T/20/80/10), ISD 100, P(W/110/10)×5 P(W/110/10)×3
PP(T/4/80/10), ISD 100, P(W/110/10)×5 P(W/110/10)×3
PP(T/12/80/10), ISD 100, P(W/110/10)×5 P(W/110/10)×3
PP(T/12/80/10), ISD 100, P(W/110/10)×5 P(W/110/10)×3
PP(T/4/80/10), ISD 100, P(W/110/10)×5 P(W/110/10)×3
PP(T/20/80/10), ISD 100, P(W/110/10)×5 P(W/110/10)×3

Figure 2:
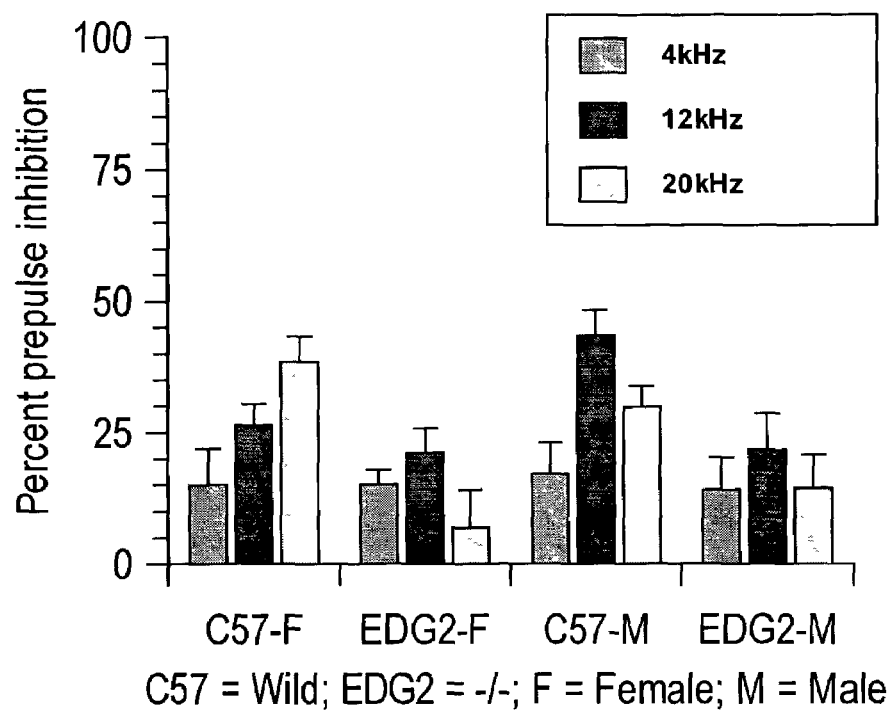
FIG. 2 shows prepulse inhibition in male and female homozygous EDG2 knockouts and wild type mice. Prepulse=80 dB tone; pulse=110 dB white noise
Figure 3:
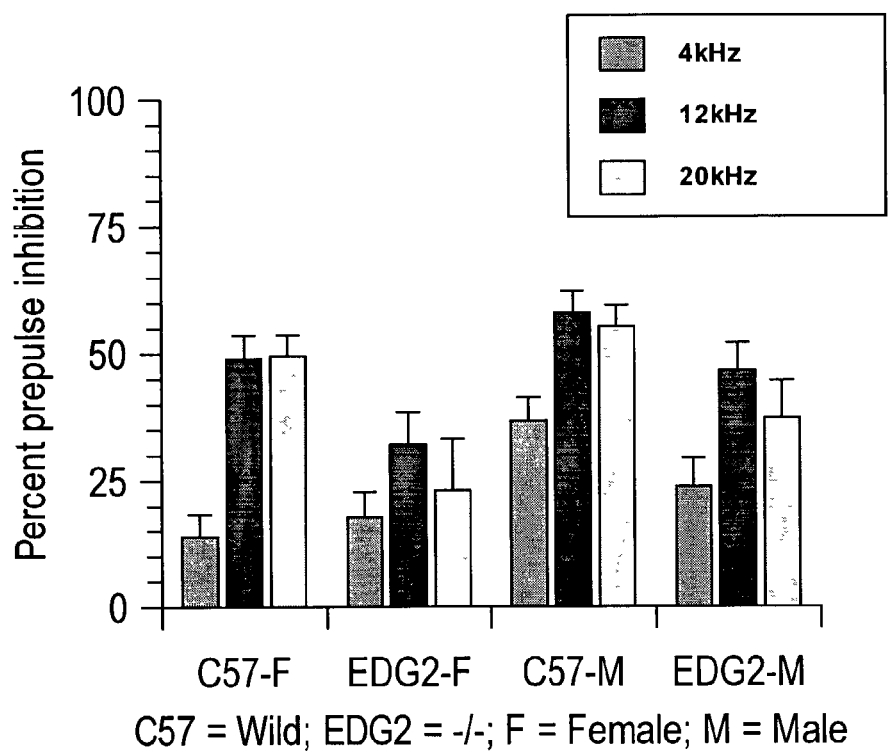
FIG. 3 shows prepulse inhibition in male and female homozygous EDG2 knockouts and wild type mice. Prepulse=90 dB tone; pulse=110 dB white noise

Thus within each session of six blocks, there were 18 pulse alone trials with the same experimental parameters, and 10 prepulse+pulse trials with the same experimental parameters. Graphical representation of data are shown as the means±1 sem of these data as shown in FIGS. 2 and 3. Data were exported to EXCEL spreadsheets and analysed by analysis of variance within Statistica™ and SAS. Between subject factors were sex and strain, and within subject factors (repeated measures design) were kHz and dB.

There were significant main effects of strain [$F(1,35)$ =12.754; $P=0.0011$], dB [$F(1,35)=49.496$; $P<0.000001$] and of kHz [$F(2,70)=25.264$; $P<0.000001$] on prepulse inhibition. There was also a significant two way interaction between dB and kHz [$F(2,72)=10.547$; $P=0.000096$], and there was a near significant effect of sex [$F(1,35)=4.062$; $P=0.052$]. There were significant two way interactions between dB and sex [$F(1,35)=4.566$; $P=0.040$], kHz and strain [$F(2,70)=7.284$; $P<0.0013$], dB and kHz [$F(2,70)$ =5.418; $P<0.006$], and significant four way interaction between dB, kHz, strain and sex [$F(2,70)=3.194$; $P<0.047$].

After combining the data for males and females, data analysis showed that the EDG2 knockout mutants showed significantly less prepulse inhibition than their C57Bl6 littermates at 80 dB/12 kHz [$P=0.0196$]; 80 dB/20 kHz [$P=0.0001$; 90 dB/12 kHz [$P=0.0149$] and 90 dB/20 kHz $P=0.0002$].

Analysis of the data for the single sexes showed that for the males, the EDG2 knockout mutants showed significantly less prepulse inhibition than their C57Bl6 littermates at 80 dB/12 kHz [$P=0.0075$] and 90 dB/20 kHz [$P=0.0251$]. There was a trend for reduced prepulse inhibition in the male EDG2 knockout mutants at 80 dB/20kHz [$P=0.0196$]; 80 dB/20 kHz. For the females, the EDG2 knockout mutants showed significantly less prepulse inhibition than their C57Bl6 littermates at 80 dB/20kHz [P=0.0002]; 90 dB/12 kHz [P=0.0403] and at 90 dB/20 kHz [P=0.0018].

Procedure for Startle

Mice were individually placed in a startle chamber and left for a pretrial delay of at least 1 minute. The mice were then exposed to a series of acoustic stimuli which were configured in one block of trials. The block consisted of the following trials:

P(4/80/10)×8, P(12/80/10)×8, P(20/80/10)×8, P(W/80/10)×8

P(4/90/10)×8, P(12/90/10)×8, P(20/90/10)×8, P(W/90/10)×8

P(4/110/10)×8, P(12/110/10)×8, P(20/110/10)×8, P(W/110/10)×8

Under the above convention, for example, P(4/80/10) consisted of a pulse of 4 kHz, 80 dB and 10 msec. Thus the block was composed of 8 trials each of a pulse (P) tone of 4, 12 or 20 kHz or white noise, at 80 or 90 or 110 dB for 10 msec giving a total of 96 trials. The order of the 96 trials within each block was fully randomised. The house light was on throughout, and there was a constant background of 60 dB white noise. The intertrial delay was set to a minimum of 15 sec and maximum of 30 sec with the trial condition set to "quiet". Under these conditions, there was a minimum trial delay of 15 sec following the preceding trial after which the next trial was triggered at the moment when the subject was not moving within the following 15 sec.

EDG2 knockout mice at 80 dB/white noise, 80 dB/12 kHz, 80 dB/20 kHz, 90 dB/white noise, 90 dB/12 kHz and 90 dB/20 kHz, but also in the male EDG2 knockout mice at 80 dB/12 kHz.

Thus the homozygous EDG2 receptor knockout caused a deficit in prepulse inhibition or startle compared to the C57Bl6 wildtype littermates.

3. Neurochemical Analysis of EDG2 Knockout Mice

Upon completion of behavioural testing, female EDG2 mice brain tissue samples were dissected from the dorsal striatum, nucleus accumbens, hippocampus, hypothalamus, cerebellum and frontal cortex (both left and right hemispheres) and snap frozen in 1.5 ml Eppendorf sample tubes on cardice and stored at −80° C. until assay. The frozen samples were then transferred into a pre-weighed 1.5 ml Eppendorf sample tube. A volume of 10 μl of homogenising buffer (0.1% w/v Na Metabisulphite, 0.01% w/v EDTA, 0.1% w/v L-cysteine, 0.4M Perchloric Acid) per mg of tissue was then added to each sample region and sonicated using an soniprep 150 (Gallenkamp, Fisons Instruments, Crawley, Sussex). A volume of the resultant slurry was put into a 1.5 ml Eppendorf and spun on a centrifuge (Labofuge 400R, Heraeus Instruments, Germany) at 10,000 rpm, 4° C. for 10 minutes. After centrifugation, 20 μl of the clear supernatant layers were put into a limited volume glass vial (0.2 ml borate silica vials, Chromacol, UK). Vials were then placed into a cooled autosampler tray (832 Temperature regulator, Gilson, France) at 4° C. and run on the HPLC system. Measurements were taken of several neurochemicals, and the results can be seen in table 1.

TABLE 1

Neurochemcial indexes were assessed in the frontal cortex (FC), hippocampus (HIPP), hypothalamus (HYPO), nucleus accumbens (NAC) and dorsal striatum. Data are mean ± SEM a: p < 0.050, b: p < 0.010 denotes significant changes in Knockout (KO) vs. Wild-type (WT) mice

| | Brain Region | | | | | | | | | |
|---|---|---|---|---|---|---|---|---|---|---|
| | FC | | Hipp | | Hypo | | NAC | | Striatum | |
| Amine | KO | WT | KO | WT | KO | WT | KO | WT | KO | WT |
| 5HIAA | 216.8 ± 10.33 b ↓ | 268.4 ± 12.66 | 421.5 ± 42.17 b ↓ | 599.3 ± 33.67 | 431.0 ± 38.63 a ↓ | 606.6 ± 62.60 | 279.2 ± 49.95 a ↓ | 417.1 ± 20.83 | 69.42 ± 22.04 | 65.79 ± 10.18 |
| 5HT | 631.1 ± 6.006 | 608.9 ± 19.14 | 487.0 ± 44.41 | 542.9 ± 20.37 | 953.4 ± 69.35 | 964.0 ± 77.95 | 720.6 ± 60.25 | 679.3 ± 56.89 | 242.1 ± 52.98 | 272.5 ± 35.64 |
| DA | 142.4 ± 119.1 | 22.42 ± 5.618 | 15.08 ± 4.333 | 25.40 ± 15.40 | 351.6 ± 18.13 | 420.9 ± 55.40 | 4833.3 ± 697.4 | 5876.0 ± 670.8 | 8236.0 ± 1648.0 a ↑ | 9324.9 ± 167.2 |
| 5-HIAA/5-HT | 0.344 ± 0.018 b ↓ | 0.441 ± 0.014 | 0.876 ± 0.057 b ↓ | 1.103 ± 0.038 | 0.541 ± 0.060 b ↓ | 0.627 ± 0.033 | 0.371 ± 0.054 b ↓ | 0.628 ± 0.042 | 0.782 ± 0.518 | 0.249 ± 0.027 |
| Dopac/DA | 1.236 ± 0.338 | 1.914 ± 0.230 | 1.973 ± 0.745 | 2.171 ± 0.494 | 0.274 ± 0.022 | 0.276 ± 0.022 | 0.137 ± 0.012 | 0.115 ± 0.017 | 0.155 ± 0.008 | 0.164 ± 0.005 |
| HVA/DA | 2.244 ± 0.814 | 4.328 ± 0.688 | 1.620 ± 0.382 | 2.618 ± 0.613 | 0.267 ± 0.044 | 0.302 ± 0.030 | 0.125 ± 0.016 | 0.144 ± 0.010 | 0.413 ± 0.236 | 0.157 ± 0.010 |
| Dopac/HVA | 0.686 ± 0.096 | 0.457 ± 0.034 | 1.187 ± 0.199 | 0.852 ± 0.058 | 1.049 ± 0.104 | 0.931 ± 0.053 | 1.199 ± 0.177 | 0.803 ± 0.115 | 0.897 ± 0.081 | 1.059 ± 0.064 |

Figure 4:
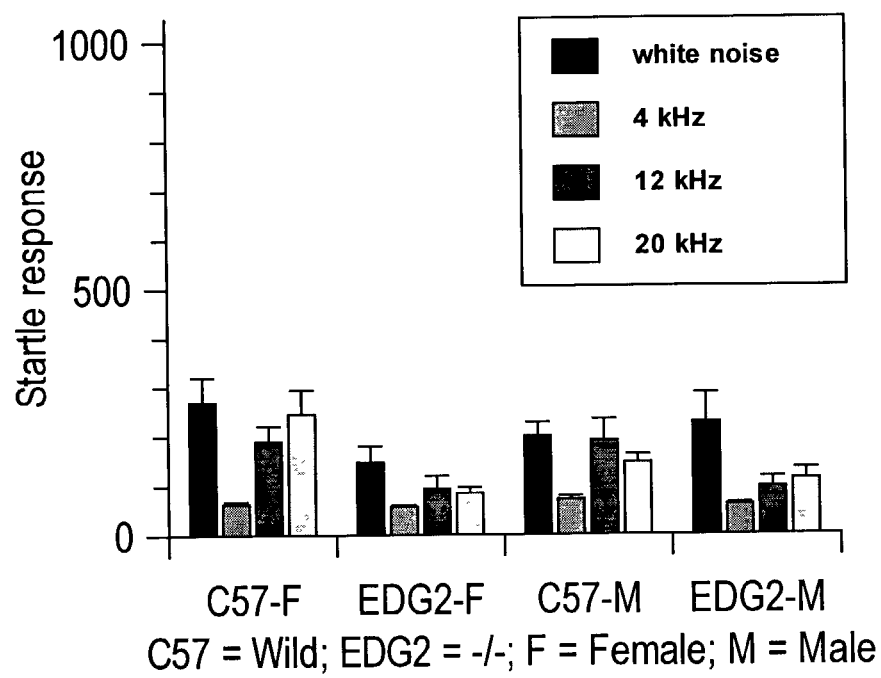
FIG. 4 shows the Startle response in Male and Female EDG2 homozygous knockouts and wild type mice. Pulse=80 dB
Figure 5:
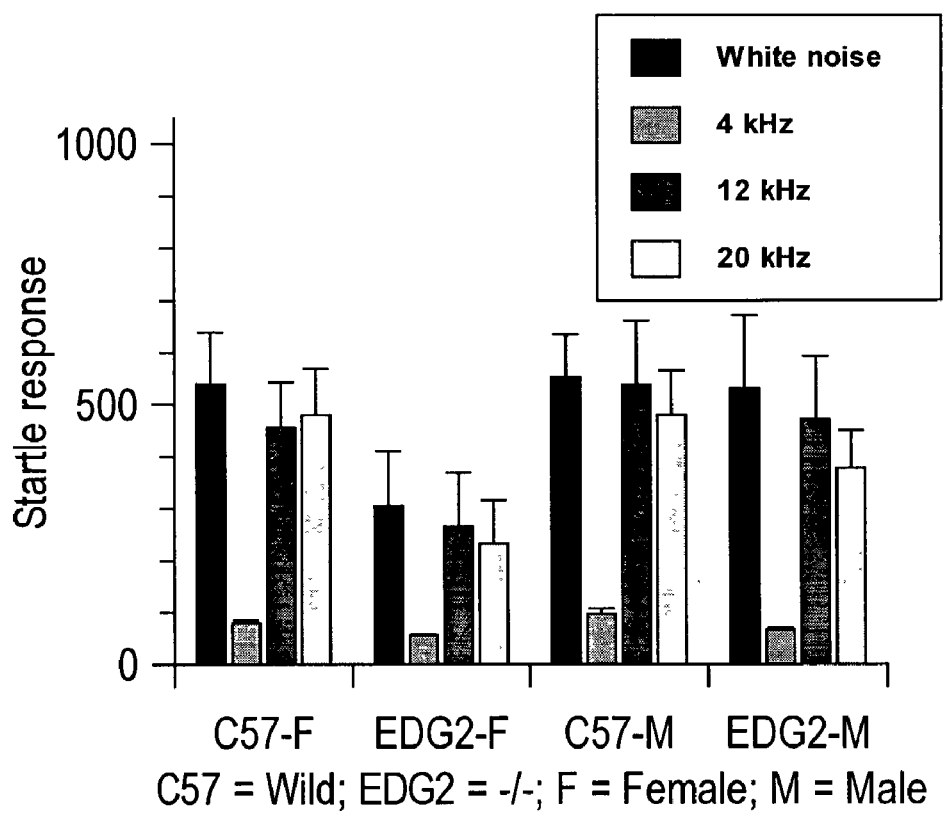
FIG. 5 shows the Startle response in Male and Female EDG2 homozygous knockouts and wild type mice. Pulse=90 dB
Figure 6:
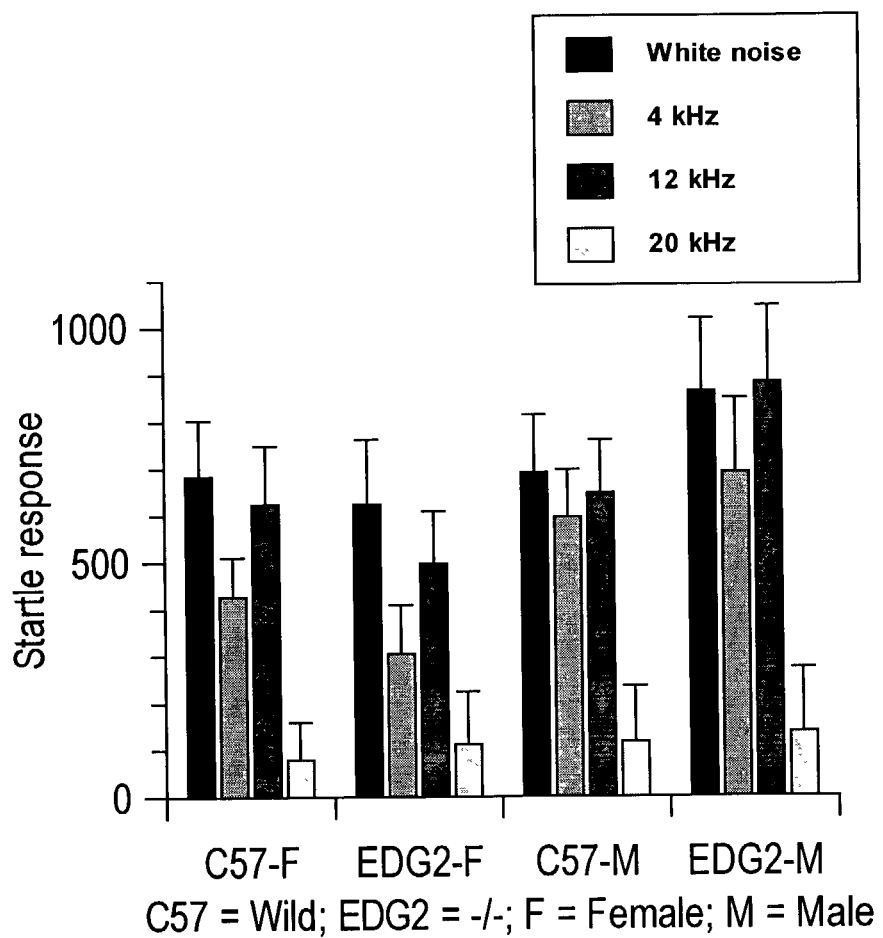
FIG. 6 shows the Startle response in Male and Female EDG2 homozygous knockouts and wild type mice. Pulse=110 dB.

Data are represented graphically in FIGS. 4, 5 and 6. Statistical diagnostics showed that log transformation of the data improved variance homogeneity. There was no main effect of sex [$F(1,35)=2.35$; $P=0.134$], on startle response. However, there were main effects of strain [$F(1,35)=4.21$; $P<=0.048$, dB [$F(2,70)=197.20$; $P=0.0001$] and of kHz [$F(3,315)=146.88$; $P=0.0001$] on startle response. There was also a significant two way interaction between strain and dB [$F(2,70)=5.69$; $P=0.0051$], sex and dB [$F(2,70)=3.78$; $P=0.0275$] and dB and kHz [$F(6,315)=20.24$; $P<0.0001$]. Reduced startle response was seen primarily in the female Overall the neurochemistry data tabulated in table 1 show a significant and selective decrease in the 5-HIAA/5-HT ratio (which is a measure of 5-HT utilisation) in the frontal cortex, dorsal hippocampus, hypothalamus and nucleus accumbens of knockouts vs. wildtype mice. The decrease in 5-HIAA/5-HT ratio was largely due to decreases in levels of 5-HIAA. Low levels of 5-HIAA have been seen in cerebrospinal fluid of people suffering from either aggression, impulsivity, depression or personality disorders (Depue and Spoont, Annal of the New York Academy of Science 487: 47–62 (1986): Rydin et al., Psychiatry Research 7:229–243

(1982); Asberg et al, 1976), disorders which are often associated with schizophrenia. In addition, the observed reduction in 5-HIAA levels is the opposite to that seen after treatment with antipsychotic compounds in the rat medial prefrontal cortex. Risperidone and amperozide, as well as clozapine and ritanserin to a lesser extent, have been shown to elevate 5-HIAA levels in this region of the brain whilst having no effect on 5-HIAA levels in the striatum (Hertel et al., Psychopharmacology 124: 74–86 (1996)). Furthermore, clozapine has been shown to elevate both 5-HT and 5-HIAA levels in plasma of schizophrenic patients (Dursun et al., Journal of Psychiatry and Neuroscience 25:347–52 (2000)).

Reduction in metabolism of 5-HT has been observed in the nucleus accumbens, hippocampus and prefrontal cortex of rats reared in isolation—a putative model of schizophrenia (Wright et al., J. Neuroscience Methods 29:283 (1989); Bickerdike et al., Behavioural Pharmacology 4:231–36 (1993); Wilkinson et al., Neuropsychopharmacology 10:61–72 (1994); Robbins et al., J. Psychopharmacology 10:39–47 (1996)). Rats reared in isolation have been shown to have deficits in prepulse inhibition which are thought to model the sensorimotor gating deficits observed in schizophrenic patients (Cilia et al., Psychopharmacology 156: 327–337 (2001)). Pharmacological studies investigating the effects of enhancing or reducing 5-HT neurotransmission show that both increases and decreases in 5-HT activity disrupt PPI (Fletcher et al., Neuropsyuchopharmacology 124: 74–86 (2001); Kehne et al., Psychopharmacology 124: 96–106 (1996)). Therefore it is possible that the changes observed in the neurochemistry of the EDG2 knockout mice could contribute to the disruption of PPI observed in these mice.

Microdialysis studies in isolated rats have shown an elevation in dopamine release in both caudate putamen and nucleus accumbens (Robbins et al., J. Psychopharmacology 10:39–47 1996) The increase in levels of DA observed in the dorsal striatum (but not nucleus accumbens) of EDG2 knockout mice vs. wildtype may reflect selective activation of the nigrostriatal dopaminergic pathway.

The invention claimed is:

1. A method of evaluating a therapeutic agent for use in the treatment of schizophrenia, the method comprising:
   i) administering the agent to a transgenic mouse whose genome comprises a homozygous, targeted gene disruption of the Endothelial differentiation gene 2 (EDG2), wherein the homozygous disruption causes a loss of functional EDG2 expression and a decreased prepulse inhibition response, and
   ii) evaluating the effect of the agent on the mouse wherein an increase in prepulse inhibition response in the mouse administered the agent is indicative of an agent that is therapeutic for use in the treatment of schizophrenia.

2. The method according to claim 1 wherein said targeted disruption disrupts the EDG2 gene such that no EDG2 protein is expressed.

3. The method according to claim 1 wherein the therapeutic agent has the ability to reverse a deficit in prepulse inhibition.

* * * * *